United States Patent
Gros et al.

(10) Patent No.: US 10,679,346 B2
(45) Date of Patent: Jun. 9, 2020

(54) SYSTEMS AND METHODS FOR CAPTURING DEEP LEARNING TRAINING DATA FROM IMAGING SYSTEMS

(71) Applicant: General Electric Company, Schenectady, NY (US)

(72) Inventors: Eric Michael Gros, Waukesha, WI (US); David Erik Chevalier, Menomonee Falls, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 173 days.

(21) Appl. No.: 15/884,151

(22) Filed: Jan. 30, 2018

(65) Prior Publication Data

US 2019/0236774 A1 Aug. 1, 2019

(51) Int. Cl.
| | |
|---|---|
| *A61B 5/00* | (2006.01) |
| *G06T 7/00* | (2017.01) |
| *G06N 3/08* | (2006.01) |
| *G16H 30/20* | (2018.01) |
| *G06K 9/46* | (2006.01) |
| *G06K 9/62* | (2006.01) |
| *G06N 3/02* | (2006.01) |

(52) U.S. Cl.
CPC .......... *G06T 7/0012* (2013.01); *G06K 9/4628* (2013.01); *G06K 9/6273* (2013.01); *G06K 9/6274* (2013.01); *G06N 3/084* (2013.01); *G16H 30/20* (2018.01); *G06K 9/6267* (2013.01); *G06T 2207/10081* (2013.01); *G06T 2207/10116* (2013.01); *G06T 2207/20081* (2013.01)

(58) Field of Classification Search
CPC ............... G06K 9/00; G06N 3/00; G06T 7/00
USPC ....................................................... 382/131
See application file for complete search history.

(56) References Cited

U.S. PATENT DOCUMENTS

2018/0204062 A1* 7/2018 Krishnakumar ... G06K 9/00624

OTHER PUBLICATIONS

Yosinski, J. et al., "How transferable are features in deep neural networks?," Proceedings of the 2014 Advances in Neural Information Processing Systems 27 (NIPS '14), Dec. 8, 2014, Montréal, Canada, 14 pages.

(Continued)

*Primary Examiner* — Abolfazl Tabatabai
(74) *Attorney, Agent, or Firm* — McCoy Russell LLP

(57) ABSTRACT

Methods and systems are provided for capturing deep learning training data from imaging systems. In one embodiment, a method for an imaging system comprises performing a scan of a subject to acquire imaging data, inputting the imaging data to a deep neural network, displaying an output of the deep neural network and an image reconstructed from the imaging data, and transmitting an intermediate representation of the imaging data generated by the deep neural network to a server for training a central deep neural network. In this way, imaging data may be leveraged for training and developing global deep learning models without transmitting the imaging data itself, thereby preserving patient privacy.

19 Claims, 4 Drawing Sheets

(56) References Cited

OTHER PUBLICATIONS

Karn, U., "An Intuitive Explanation of Convolutional Neural Networks," The Data Science Blog Website, Available Online at https://ujjwalkarn.me/2016/08/11/intuitive-explanation-convnets/, Aug. 11, 2016, 21 pages.

Beaulieu-Jones, B. et al., "Privacy-preserving generative deep neural networks support clinical data sharing," bioRxiv Website, Available Online at https://www.biorxiv.org/content/early/2017/11/15/159756, Available as Early as Jul. 5, 2017, 16 pages.

\* cited by examiner

SYSTEMS AND METHODS FOR CAPTURING DEEP LEARNING TRAINING DATA FROM IMAGING SYSTEMS

FIELD

Embodiments of the subject matter disclosed herein relate to non-invasive diagnostic imaging, and more particularly, to the generating deep learning training data with an imaging system.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior or the human body or of other imaged structures).

New post-processing techniques can substantially improve the functionality of an imaging system as well as the accuracy of clinical diagnoses. For example, modern deep learning techniques may allow lesions to be accurately detected in tomographic images with a lower image quality, thereby enabling a reduction in radiation dose (and thus a potential reduction in image quality) without sacrificing the diagnostic effectiveness of the imaging system. One notable feature of deep learning algorithms is the ability for the algorithm to improve over time as it is trained on additional imaging data acquired by the imaging system. However, it is difficult to leverage these improvements for other imaging systems, as training the deep learning algorithm typically requires access to the raw imaging data, which potentially includes sensitive patient information.

BRIEF DESCRIPTION

In one embodiment, a method for an imaging system comprises performing a scan of a subject to acquire imaging data, inputting the imaging data to a deep neural network, displaying an output of the deep neural network and an image reconstructed from the imaging data, and transmitting an intermediate representation of the imaging data generated by the deep neural network to a server for training a central deep neural network. In this way, imaging data may be leveraged for training and developing global deep learning models without transmitting the imaging data itself, thereby preserving patient privacy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of non-invasive diagnostic imaging. In particular, systems and methods are provided for collecting training data from one or more imaging systems for training a central deep learning algorithm. An example system that may be used to collect deep learning training data from a plurality of imaging systems is provided in FIG. 1. A deep neural network, such as the deep neural network depicted in FIG. 2, installed in an imaging system generates an intermediate representation of imaging data. A deep neural network, such as the deep neural network depicted in FIG. 3, installed in a central server uses the intermediate representation of the imaging data as input features. A method for generating training data, such as the method shown in FIG. 4, includes transmitting the intermediate representation and a ground truth from the imaging system to the server. A method for training a central deep learning model, such as the method shown in FIG. 5, includes training the central deep learning model using the intermediate representation and the ground truth. An example CT imaging system that may be used to acquire images and generate training data in accordance with the present techniques is provided in FIGS. 6 and 7.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

Figure 1:
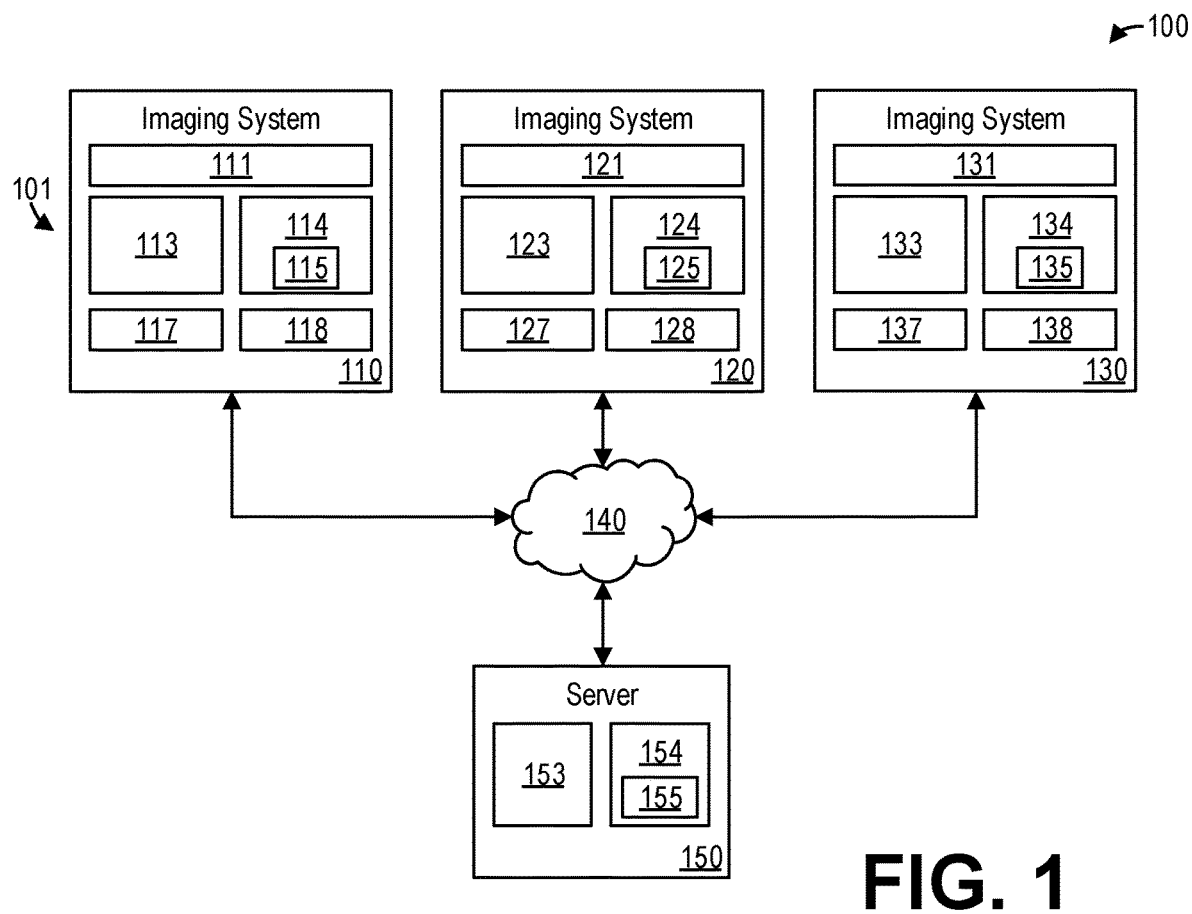
FIG. 1 shows a block schematic diagram of an example system for deep learning training data collection according to an embodiment.

FIG. 1 shows a schematic block diagram illustrating an example system 100 for training a centralized learning model with data from a plurality of imaging systems in accordance with an embodiment. The components of system 100 are depicted at a high-level to emphasize components of the system 100 that are relevant to the present disclosure, though it should be understood that the system 100 may include additional systems and components not depicted in FIG. 1.

The system 100 includes a plurality of imaging systems 101, including at least a first imaging system 110, a second imaging system 120, and a third imaging system 130. Though only three imaging systems 110, 120, and 130 are depicted, it should be appreciated that the plurality of imaging systems 101 may include any number of imaging systems. Each imaging system of the plurality of imaging systems may be located in different hospitals or other institutions.

Furthermore, the plurality of imaging systems 101 may comprise a same imaging modality. For example, each imaging system of the plurality of imaging systems 101 may comprise a CT imaging system. An example CT imaging system is described further herein with regard to FIGS. 5 and 6. As another example, each imaging system of the plurality of imaging systems 101 may comprise a magnetic resonance imaging (MRI) system. As yet another example, each imaging system of the plurality of imaging systems 101 may comprise a positron emission tomography (PET) imaging system. As another example, each imaging system of the plurality of imaging systems 101 may comprise an ultrasound imaging system. In some examples, the plurality of imaging systems may comprise a multi-modality imaging system. For example, each imaging system of the plurality of imaging systems 101 may comprise a PET/CT imaging system.

The first imaging system 110 comprises a scanner 111, a processor 113, a non-transitory memory 114, a user interface 117, and a display device 118. The scanner 111 comprises the components of the first imaging system 110 configured to scan or image a subject. For example, if the first imaging system 110 comprises a CT imaging system, the scanner 111 comprises at least an x-ray tube and a detector, and in some examples may further comprise a gantry, a digital acquisition system (DAS), and other components necessary for scanning or imaging a subject. Additional components of a CT imaging system that may comprise the scanner 111 are described further herein with regard to FIGS. 5 and 6. As another example, if the first imaging system 110 comprises an ultrasound imaging system, the scanner 111 comprises at least an ultrasound transducer. Similar to the first imaging system 110, the second imaging system 120 includes a scanner 121, a processor 123, a non-transitory memory 124, a user interface 127, and a display device 128. Further, the third imaging system 130 comprises a scanner 131, a processor 133, a non-transitory memory 134, a user interface 137, and a display device 138.

Each imaging system of the plurality of imaging systems 101 includes a neural network trained to perform a task, including but not limited to image classification. As depicted, the first imaging system 110 includes a first neural network 115 stored in the non-transitory memory 114, the second imaging system 120 includes a second neural network 125 stored in the non-transitory memory 124, and the third imaging system 130 includes a third neural network 135 stored in the non-transitory memory 134.

Initially, the first neural network 115, the second neural network 125, and the third neural network 135 may comprise a same neural network. Over time, as the different imaging systems 110, 120, and 130 are used to image subjects and the corresponding neural networks 115, 125, and 135 are used to process the images or imaging data, the knowledge of the neural networks 115, 125, and 135 diverges. That is, the first neural network 115 is trained over time using imaging data acquired by the imaging system 110, the second neural network 125 is trained over time using imaging data acquired by the imaging system 120, and the third neural network 135 is trained over time using imaging data acquired by the imaging system 130.

The system 100 further comprises a server 150 configured to collect data from the plurality of imaging systems 101 for training a central deep neural network 155. To that end, the server 150 comprises a processor 153 and a non-transitory memory 154 with the central deep neural network 155 stored thereon. Further, as the server 150 may be located at a different geographical location than the plurality of imaging systems 101, each imaging system of the plurality of imaging systems 101 is communicatively coupled to the server 150 via a network 140 such as the Internet. The central deep neural network 155 initially comprises the same neural network model as the first deep neural network 115, the second deep neural network 125, and the third deep neural network 135.

As discussed further herein, the server 150 aggregates training data received via the network 140 from each of the plurality of imaging systems 101 and trains the central deep neural network 155. After training the central neural network 155, the central deep neural network 155 is deployed to the plurality of imaging systems 101 to replace or update the deep neural networks 115, 125, and 135.

Figure 2:
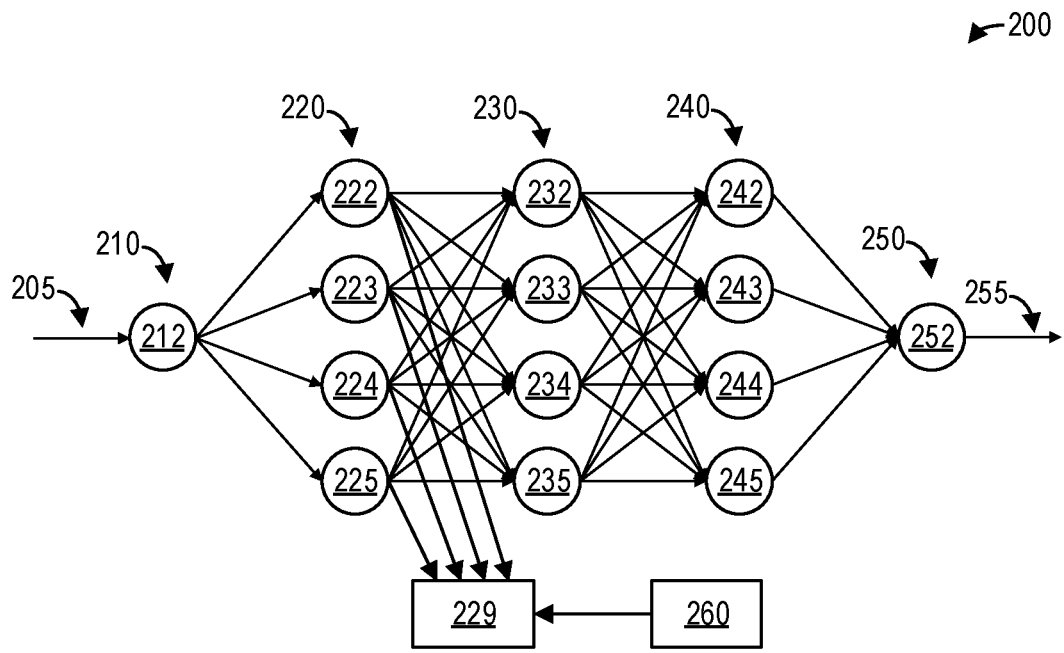
FIG. 2 shows a high-level diagram illustrating an example deep neural network for an imaging system according to an embodiment.

FIG. 2 shows a high-level diagram illustrating an example deep neural network 200 according to an embodiment. The deep neural network 200 may comprise the deep neural networks 115, 125, and 135 described hereinabove with regard to FIG. 1. As such, the deep neural network 200 may be trained to perform a task related to diagnostic imaging, such as automatically classifying organs in an image, as an illustrative and non-limiting example.

As depicted, the deep neural network 200 includes an input layer 210, a first hidden layer 220, a second hidden layer 230, a third hidden layer 240, and an output layer 250. Input layer 210 comprises a plurality of input nodes 212. As discussed further herein, an input 205 comprising imaging data (e.g., projection data) and/or image data (e.g., an image) is input to the input layer 210. The first hidden layer 220 includes a plurality of hidden nodes 222, 223, 224, and 225. As depicted, each input node 212 is connected to each of the hidden nodes 222, 223, 224, and 225 of the first hidden layer 220. The second hidden layer 230 includes a plurality of hidden nodes 232, 233, 234, and 235. Each hidden node 222, 223, 224, and 225 of the first hidden layer 220 is connected to each hidden node 232, 233, 234, and 235 of the second hidden layer 230. The third hidden layer 240 includes a plurality of hidden nodes 242, 243, 244, and 245. Each hidden node 232, 233, 234, and 235 of the second hidden layer 230 is connected to each hidden node 242, 243, 244, and 245 of the third hidden layer 240. The output layer 250 includes a plurality of output nodes 252. Each hidden node 242, 243, 244, and 245 of the third hidden layer 240 is connected to each output node 252 of the output layer 250. The output layer 250 generates an output 255 which comprises the result of the processing by the deep neural network 200.

The hidden nodes of the hidden layers 220, 230, and 240 receive one or more inputs and sums them to produce an output. The sums of each node are weighted, and the sum is passed through a non-linear activation function. The resulting output is then passed on to each node in the following layer. The deep neural network 200 may therefore comprise a feedforward neural network. In some examples, the deep neural network 200 may learn through backpropagation. To minimize total error, gradient descent may be used to adjust each weight in proportion to the derivative of the error with respect to that weight, provided the non-linear activation functions are differentiable. Also, global optimization methods may be used to train the weights of the deep neural network 200.

The output of the hidden nodes 222, 223, 224, and 225 of the first hidden layer 220 are collected as an intermediate representation 229 of the input 205. As discussed further herein, this intermediate representation 229 may be transmitted to a central server such as server 150 for training the central deep neural network 155. As discussed further herein, the hidden nodes 222, 223, 224, and 225 of the first hidden layer 220 are not trainable or adjustable, but rather are fixed in order for the intermediate representation 229 to be usable for training the central deep neural network 155.

In addition, the ground truth 260 comprising the desired output of the DNN 200 (in contrast with the output 255) may be bundled with the intermediate representation 229 for training the central deep neural network 155. The ground truth 260 may be received, for example, via a user interface such as user interface 117 of the imaging system 110.

It should be understood that the deep neural network 200 is illustrative and non-limiting, as FIG. 2 illustrates a relatively small number of nodes for simplicity. For example, although only one input node 212 is depicted, it should be appreciated that input layer 210 may include any suitable number of input nodes 212. Similarly, although only one output node 252 is depicted, it should be appreciated that output layer 250 may include any suitable number of output nodes 252. Furthermore, three hidden layers 220, 230, and 240 are depicted in the deep neural network 200, though it should be appreciated that the deep neural network 200 may include at least two hidden layers, and in some examples may include more than three hidden layers. Furthermore, each of the hidden layers 220, 230, and 240 are depicted as comprising four hidden nodes each, though it should be appreciated that each of the hidden layers 220, 230, and 240 may include any suitable number of hidden nodes, and in some examples each hidden layer may include hundreds or even thousands of hidden nodes.

Figure 3:
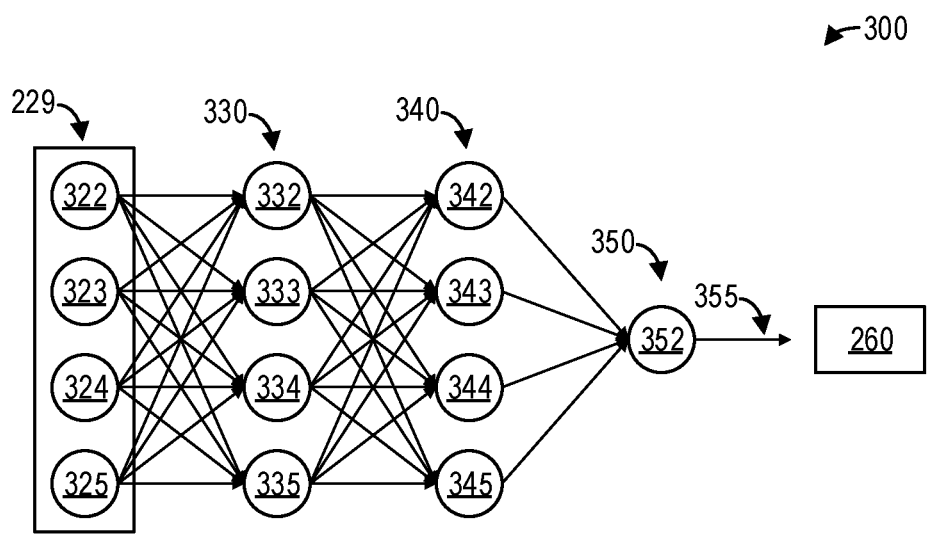
FIG. 3 shows a high-level diagram illustrating an example deep neural network for a central server according to an embodiment.

FIG. 3 shows a high-level diagram illustrating an example deep neural network 300 according to an embodiment. In particular, the deep neural network 300 may comprise the central deep neural network 155 of the server 150 described hereinabove with regard to FIG. 1. The deep neural network 300 includes a second hidden layer 330, a third hidden layer 340, and an output layer 350 that are structurally identical to the second hidden layer 230, the third hidden layer 240, and the output layer 250, respectively, of the deep neural network 200.

However, rather than an input layer similar to the input layer 210 of the deep neural network 200, which receives imaging data as an input 205, the deep neural network 300 uses the intermediate representation 229 as an input layer. As depicted, the intermediate representation 229 comprises the output of the first hidden layer 220 of the deep neural network 200. In particular, the intermediate representation 229 includes the output 322 of the hidden node 222, the output 323 of the hidden node 223, the output 324 of the hidden node 224, and the output 325 of the hidden node 225.

The outputs 322, 323, 324, and 325 are input to each of the hidden nodes 332, 333, 334, and 335 of the second hidden layer 330. Each hidden node of the second hidden layer 330 receives the inputs from the intermediate representation 229 and sums them to produce an output. The sums of each node are weighted, and the sum is passed through a non-linear activation function. The resulting output is then passed on to each of the hidden nodes 342, 343, 344, and 345 in the following hidden layer 340. Each hidden node of the third hidden layer 340 receives the inputs from the second hidden layer 330 and sums them to produce an output, the sums of each node are weighted, the sum is passed through a non-linear activation function, and the resulting output is then passed onto each of the nodes 352 of the output layer 350. The nodes 352 of the output layer 350 in turn generate a final output 355 of the deep neural network 300.

The output 355 is compared to the ground truth 260 to determine a loss function, and backpropagation is performed with the loss function to adjust the weights of the nodes of the output layer 350, the third hidden layer 340, and the second hidden layer 330. In this way, the deep neural network 300 is trained using the intermediate representation 229 of the imaging data and the ground truth 260.

The layer of the deep neural network 300 comprising the intermediate representation 229 is not trainable or adjustable in the backpropagation process, although all other layers of the deep neural network 300, including the second hidden layer 330, the third hidden layer 340, and the output layer 350 are trainable. The ability to train the deep neural network 300 with the intermediate representation 229 relies on the fixed state (i.e. untrainability) of the layer comprising the intermediate representation 229 of the deep neural network 300 as well as the first hidden layer 220 of the deep neural network 200. In other words, using the intermediate representation 229 as the input to the second hidden layer 330 is equivalent to using the input 205, the input layer 210, and the first hidden layer 220 of the deep neural network 200 as the input to the second hidden layer 330. By providing the central deep neural network 155 with the architecture of the deep neural network 300, and by providing the deep neural networks 115, 125, and 135 with the architecture of the deep neural network 200, the central deep neural network 155 may be trained on imaging data acquired by the plurality of imaging systems 101 by training the central deep neural network 155 with the intermediate representations generated by the deep neural networks 115, 125, and 135.

Figure 4:
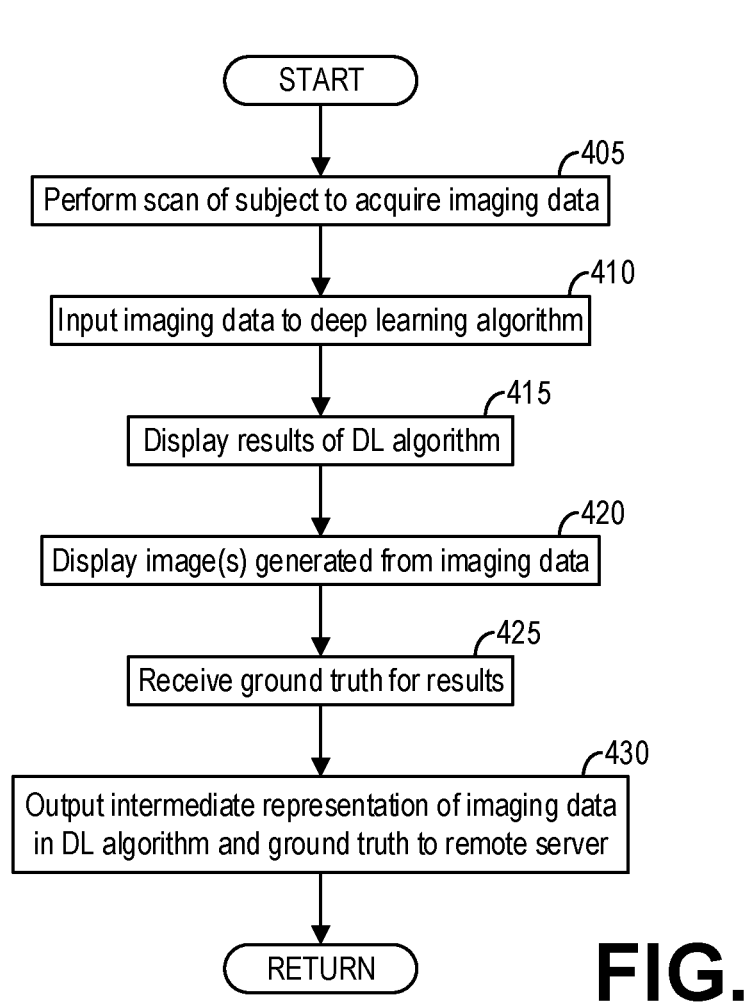
FIG. 4 shows a high-level flowchart illustrating an example method for generating deep learning training data with an imaging system according to an embodiment.

FIG. 4 shows a high-level flowchart illustrating an example method 400 for generating deep learning training data with an imaging system according to an embodiment. In particular, method 400 relates to outputting the outputs of hidden nodes of a first hidden layer of a deep neural network to a central server for training a central deep neural network. Method 400 is described with regard to the systems and components of FIGS. 1 and 2, though it should be appreciated that the method may be implemented with other systems and components without departing from the scope of the present disclosure. Method 400 may be implemented as executable instructions in non-transitory memory of an imaging system, such as imaging system 110, 120, and 130. For the purpose of clarity, method 400 is described herein from the perspective of imaging system 110.

Method 400 begins at 405. At 405, method 400 performs a scan of a subject to acquire imaging data. For example, method 400 may control the scanner 111 of the first imaging system 110 to scan the subject and thereby acquire imaging data. An example method for scanning a subject to acquire imaging data when the imaging system comprises a CT imaging system is described further herein with regard to FIGS. 6 and 7.

At 410, method 400 inputs the imaging data to a deep learning (DL) algorithm. As a non-limiting and illustrative example, the DL algorithm may comprise a deep neural network including two or more hidden layers, such as the deep neural network 200 described hereinabove. Thus, for example, method 400 may input the imaging data acquired at 405 to the first deep neural network 115.

At 415, method 400 displays the results of the DL algorithm. For example, if the first deep neural network 115 is configured with the architecture of the deep neural network 200, method 400 displays the output 255 generated by the first deep neural network 115 via a display device such as display device 118. Further, at 420, method 400 displays one or more images generated from the imaging data. For example, method 400 may reconstruct an image from the imaging data acquired at 405, and display the image via the display device 118. In some examples, method 400 displays the results of the DL algorithm superimposed on the image. In other examples, method 400 displays the results of the DL algorithm adjacent to the image on the display device 118.

At 425, method 400 receives a ground truth for the results. For example, an operator of the imaging system 110 may input the ground truth via user interface 117, and so method 400 receives the ground truth via the user interface 117. As discussed hereinabove, the ground truth comprises the desired output of the DL algorithm. For example, the ground truth comprises factual data regarding the output that is observed or measured by a human. In other words, the ground truth comprises the correct output that the DL algorithm ideally should have output. As an illustrative and non-limiting example, if the task of the DL algorithm is to classify organs in an image, the ground truth may comprise one or more labels of the organs in the image as identified by a human. In this example, the operator of the imaging system 110 may view the image displayed at 420 and input, via the user interface 117, the ground truth comprising labels for one or more organs visible in the image. The format of the ground truth thus corresponds to the format of the displayed output of the DL algorithm. For example, if the task of the DL algorithm is to segment organs in the image, the corresponding ground truth may comprise a segmentation of the organs in the image performed by an operator of the imaging system 110 via the user interface 117.

Method 400 may use the ground truth received at 425 to train the DL algorithm. For example, the first deep neural network 115 may be trained using backpropagation of errors determined based on the output of the first deep neural network 115 and the ground truth received at 425. As noted hereinabove with regard to FIG. 2, the first hidden layer 220 of the first deep neural network 115 may not be trained in order to maintain compatibility with the central deep neural network 155.

Continuing at 430, method 400 outputs an intermediate representation of the imaging data in the DL algorithm and the ground truth to a remote server, such as server 150. The intermediate representation may comprise any sufficient transformation of the imaging data which contains useful information for a DL algorithm while also preserving privacy. That is, the intermediate representation of the imaging data may not be transformable back into the imaging data itself, thereby preserving the privacy of the subject being imaged, but may still be used to train the central deep neural network 155. As discussed hereinabove, the intermediate representation may comprise the outputs of the first hidden layer 220 of the deep neural network 115. It should be appreciated that the intermediate representation may comprise another representation of the imaging data. For example, the intermediate representation may comprise the output of the second hidden layer 230 of the deep neural network 115. As another example, the intermediate representation may comprise the output of a generative adversarial network (GAN), or a transformation of the imaging data onto an atlas or standard reference. Method 400 then ends.

Figure 5:
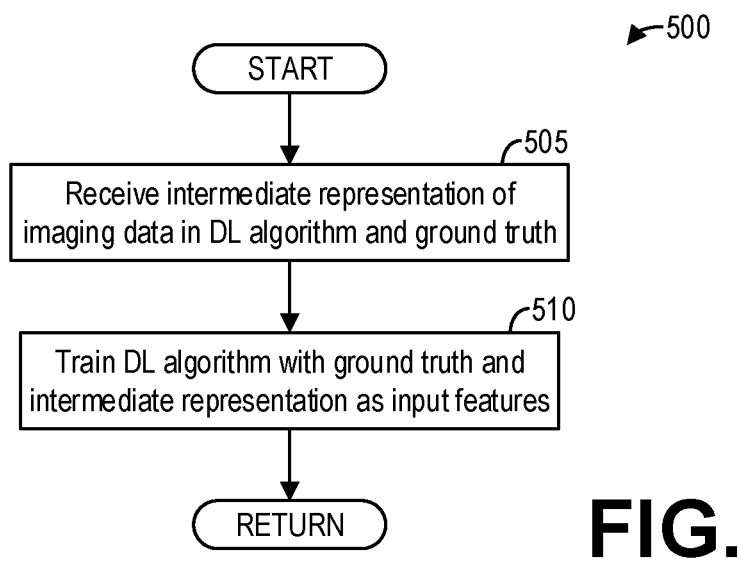
FIG. 5 shows a high-level flow chart illustrating an example method for centralized collection of deep learning training data according to an embodiment.

FIG. 5 shows a high-level flow chart illustrating an example method 500 for centralized collection of deep learning training data according to an embodiment. In particular, method 500 relates to training a central deep neural network such as central deep neural network 155 with data generated by a plurality of imaging systems 101. Method 500 is described with regard to the systems and components of FIGS. 1-3, though it should be appreciated that the method may be implemented with other systems and components without departing from the scope of the present disclosure. Method 500 may be stored as executable instructions in non-transitory memory 154 of a server 150 and may be executed by a processor 153 of the server 150.

Method 500 begins at 505. At 505, method 500 receives the intermediate representation of the imaging data in the DL algorithm and the ground truth. For example, method 500 may receive the intermediate representation of the imaging data and the corresponding ground truth output at 430 by an imaging system such as imaging system 110.

Continuing at 510, method 500 trains the central DL algorithm with the ground truth and the intermediate representation as input features. For example, method 500 may input the intermediate representation of the imaging data to the central deep neural network 155 as discussed hereinabove with regard to FIG. 3. Further, method 500 uses the ground truth to calculate a loss function for the output of the central deep neural network 155, and performs backpropagation with gradient descent to adjust the weights of the different layers of the central deep neural network 155 (excluding the input layer comprising the intermediate representation). Method 500 then ends.

Figure 6:
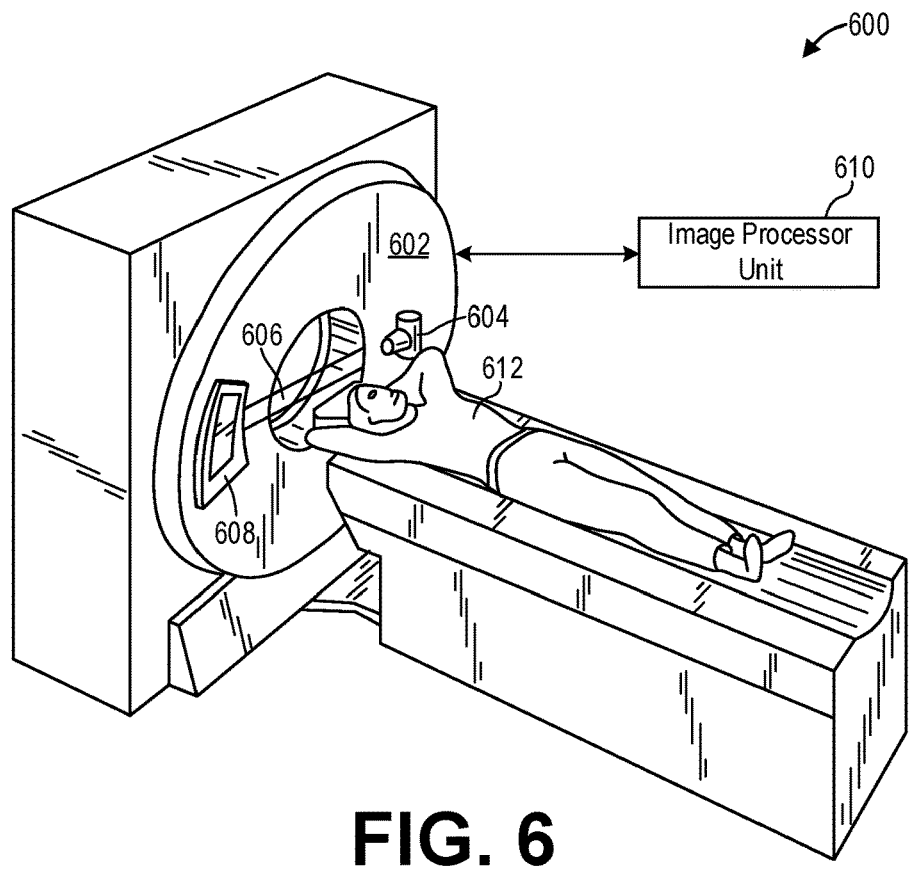
FIG. 6 shows a pictorial view of an imaging system according to an embodiment.

FIG. 6 illustrates an exemplary CT system 600 configured to allow fast and iterative image reconstruction. Particularly, the CT system 600 is configured to image a subject 612 such as a patient, an inanimate object, one or more manufactured parts, and/or foreign objects such as dental implants, stents, and/or contrast agents present within the body. In one embodiment, the CT system 600 includes a gantry 602, which in turn, may further include at least one x-ray radiation source 604 configured to project a beam of x-ray radiation 606 for use in imaging the subject 612. Specifically, the x-ray radiation source 604 is configured to project the x-rays 606 towards a detector array 608 positioned on the opposite side of the gantry 602. Although FIG. 6 depicts only a single x-ray radiation source 604, in certain embodiments, multiple x-ray radiation sources may be employed to project a plurality of x-rays 606 for acquiring projection data corresponding to the subject 612 at different energy levels.

In certain embodiments, the CT system 600 further includes an image processor unit 610 configured to reconstruct images of a target volume of the subject 612 using an iterative or analytic image reconstruction method. For example, the image processor unit 610 may use an analytic image reconstruction approach such as filtered backprojection (FBP) to reconstruct images of a target volume of the patient. As another example, the image processor unit 610 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 612.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as the patient or subject 612. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two-dimensional slice taken through the object. One method for reconstructing an image from a set of projection data is referred to in the art as the filtered backprojection (FBP) technique. Transmission and emission tomography reconstruction techniques also include statistical iterative methods such as maximum likelihood expectation maximization (MLEM) and ordered-subsets expectation reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate (or are configured to generate) at least one viewable image.

Figure 7:
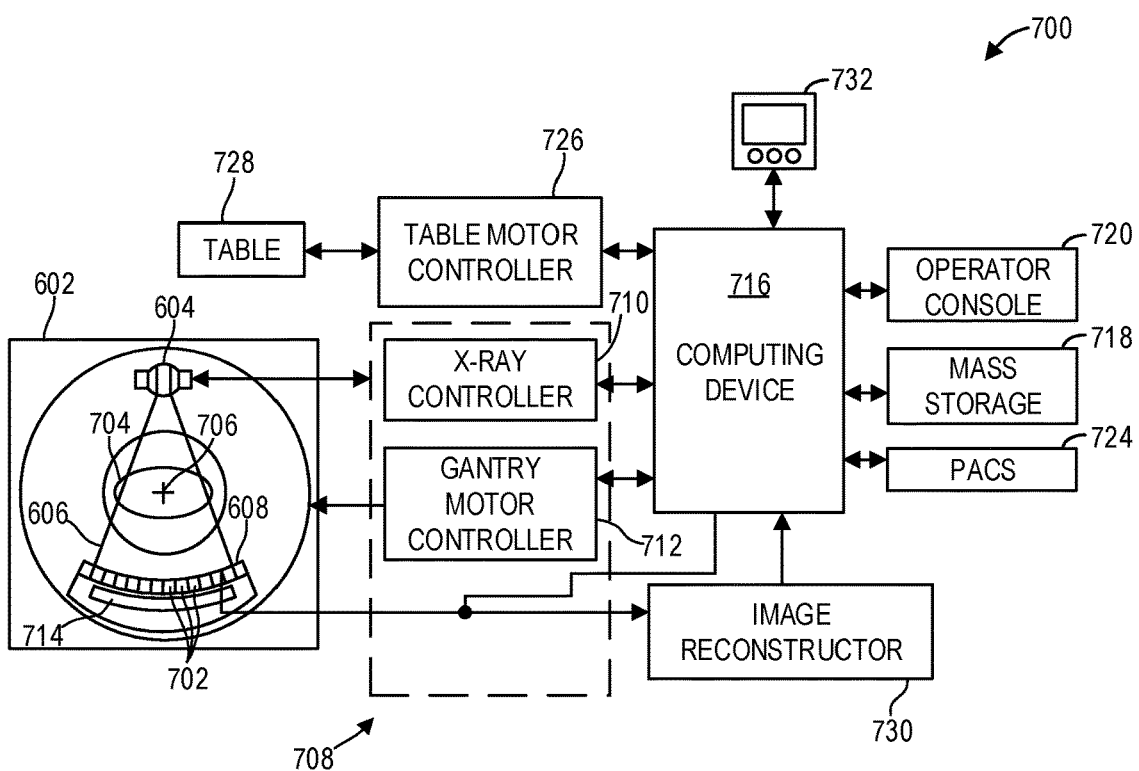
FIG. 7 shows a block schematic diagram of an exemplary imaging system according to an embodiment.

FIG. 7 illustrates an exemplary imaging system 700 similar to the CT system 600 of FIG. 6. In accordance with aspects of the present disclosure, the imaging system 700 is configured to output intermediate representations of imaging data from a deep learning algorithm to a central server. In one embodiment, the imaging system 700 includes the detector array 608 (see FIG. 6). The detector array 608 further includes a plurality of detector elements 702 that together sense the x-ray beams 606 (see FIG. 6) that pass through a subject 704 such as a patient to acquire corresponding projection data. Accordingly, in one embodiment, the detector array 608 is fabricated in a multi-slice configuration including the plurality of rows of cells or detector elements 702. In such a configuration, one or more additional rows of the detector elements 702 are arranged in a parallel configuration for acquiring the projection data.

In certain embodiments, the imaging system 700 is configured to traverse different angular positions around the subject 704 for acquiring desired projection data. Accordingly, the gantry 602 and the components mounted thereon may be configured to rotate about a center of rotation 706 for acquiring the projection data, for example, at different energy levels. Alternatively, in embodiments where a projection angle relative to the subject 704 varies as a function of time, the mounted components may be configured to move along a general curve rather than along a segment of a circle.

As the x-ray radiation source 604 and the detector array 608 rotate, the detector array 608 collects data of the attenuated x-ray beams. The data collected by the detector array 608 undergoes pre-processing and calibration to condition the data to represent the line integrals of the attenuation coefficients of the scanned subject 704. The processed data are commonly called projections.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube kVp level or spectrum with an energy resolving detector of the detector array 608.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 700 reveals internal features of the subject 704, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 700 includes a control mechanism 708 to control movement of the components such as rotation of the gantry 602 and the operation of the x-ray radiation source 604. In certain embodiments, the control mechanism 708 further includes an x-ray controller 710 configured to provide power and timing signals to the x-ray radiation source 604. Additionally, the control mechanism 708 includes a gantry motor controller 712 configured to control a rotational speed and/or position of the gantry 602 based on imaging requirements.

In certain embodiments, the control mechanism 708 further includes a data acquisition system (DAS) 714 configured to sample analog data received from the detector elements 702 and convert the analog data to digital signals for subsequent processing. The data sampled and digitized by the DAS 714 is transmitted to a computer or computing device 716. In one example, the computing device 716 stores the data in a storage device such as mass storage 718. The mass storage 718, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 716 provides commands and parameters to one or more of the DAS 714, the x-ray controller 710, and the gantry motor controller 712 for controlling system operations such as data acquisition and/or processing. In certain embodiments, the computing device 716 controls system operations based on operator input. The computing device 716 receives the operator input, for example, including commands and/or scanning parameters via an operator console 720 operatively coupled to the computing device 716. The operator console 720 may include a keyboard (not shown) and/or a touchscreen to allow the operator to specify the commands and/or scanning parameters.

Although FIG. 7 illustrates only one operator console 720, more than one operator console may be coupled to the imaging system 700, for example, for inputting or outputting system parameters, requesting examinations, and/or viewing images. Further, in certain embodiments, the imaging system 700 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 700 either includes or is coupled to a picture archiving and communications system (PACS) 724. In an exemplary implementation, the PACS 724 is further coupled to a remote system such as a radiology department information system, hospital information system, and/or to an internal or external network (not shown) to allow operators at different locations to supply commands and parameters and/or gain access to the image data.

The computing device 716 uses the operator-supplied and/or system-defined commands and parameters to operate a table motor controller 726, which in turn, may control a table 728 which may comprise a motorized table. Particularly, the table motor controller 726 moves the table 728 for appropriately positioning the subject 704 in the gantry 602 for acquiring projection data corresponding to the target volume of the subject 704.

As previously noted, the DAS 714 samples and digitizes the projection data acquired by the detector elements 702. Subsequently, an image reconstructor 730 uses the sampled and digitized x-ray data to perform high-speed reconstruction. Although FIG. 7 illustrates the image reconstructor 730 as a separate entity, in certain embodiments, the image reconstructor 730 may form part of the computing device 716. Alternatively, the image reconstructor 730 may be absent from the imaging system 700 and instead the computing device 716 may perform one or more of the functions of the image reconstructor 730. Moreover, the image reconstructor 730 may be located locally or remotely, and may be operatively connected to the imaging system 700 using a wired or wireless network. Particularly, one exemplary embodiment may use computing resources in a "cloud" network cluster for the image reconstructor 730.

In one embodiment, the image reconstructor 730 stores the images reconstructed in the storage device or mass storage 718. Alternatively, the image reconstructor 730 transmits the reconstructed images to the computing device 716 for generating useful patient information for diagnosis and evaluation. In certain embodiments, the computing device 716 transmits the reconstructed images and/or the patient information to a display 732 communicatively coupled to the computing device 716 and/or the image reconstructor 730.

The various methods and processes described further herein may be stored as executable instructions in non-transitory memory on a computing device in imaging system 700. For example, image reconstructor 730 may include such executable instructions in non-transitory memory, and may apply the methods described herein to reconstruct an image from scanning data. In another embodiment, computing device 716 may include the instructions in non-transitory memory, and may apply the methods described herein, at least in part, to a reconstructed image after receiving the reconstructed image from image reconstructor 730. In yet another embodiment, the methods and processes described herein may be distributed across image reconstructor 730 and computing system 716.

In one embodiment, the display 732 allows the operator to evaluate the imaged anatomy. The display 732 may also allow the operator to select a volume of interest (VOI) and/or request patient information, for example, via a graphical user interface (GUI) for a subsequent scan or processing.

A technical effect of the disclosure is the transmission of an intermediate representation of imaging data to a server for training a deep neural network. Another technical effect of the disclosure is the acquisition of imaging data and the training of a deep neural network with the imaging data.

In one embodiment, a method for an imaging system comprises performing a scan of a subject to acquire imaging data, inputting the imaging data to a deep neural network, displaying an output of the deep neural network and an image reconstructed from the imaging data, and transmitting an intermediate representation of the imaging data generated by the deep neural network to a server for training a central deep neural network.

In a first example of the method, the deep neural network comprises a first hidden layer and a second hidden layer, and the intermediate representation comprises an output of the first hidden layer. In a second example of the method optionally including the first example, the method further comprises training the deep neural network based on an error of the output of the deep neural network, wherein training the deep neural network comprises adjusting weights of hidden nodes of the second hidden layer. In a third example of the method optionally including one or more of the first and second examples, training the deep neural network excludes training the first hidden layer. In a fourth example of the method optionally including one or more of the first through third examples, the method further comprises receiving a ground truth for the deep neural network, and transmitting the ground truth to the server for training the central deep neural network. In a fifth example of the method optionally including one or more of the first through fourth examples, the ground truth is received from a user via a user interface of the imaging system. In a sixth example of the method optionally including one or more of the first through fifth examples, the method further comprises training the deep neural network with backpropagation based on the ground truth. In a seventh example of the method optionally including one or more of the first through sixth examples, the method further comprises reconstructing the image from the imaging data, wherein inputting the imaging data to the deep neural network comprises inputting the image to the deep neural network. In an eighth example of the method optionally including one or more of the first through seventh examples, displaying the output of the deep neural network and the image comprises displaying, via a display device of the imaging system, the output superimposed on the image. In a ninth example of the method optionally including one or more of the first through eighth examples, displaying the output of the deep neural network and the image comprises displaying, via a display device of the imaging system, the output of the deep neural network adjacent to the image.

In another embodiment, a system comprises an imaging system comprising a scanner for scanning a subject to acquire imaging data, a processor, and a non-transitory memory storing a deep neural network, and a server comprising a processor and a non-transitory memory storing a central deep neural network, the server communicatively coupled to the imaging system via a network, wherein the imaging system is configured with executable instructions in the non-transitory memory of the imaging system that when executed cause the processor of the imaging system to transmit an intermediate representation of the imaging data to the server for training the central deep neural network, the intermediate representation of the imaging data generated by the deep neural network.

In a first example of the system, the imaging system further comprises a user interface configured to receive input from an operator of the imaging system, wherein the imaging system is further configured with executable instructions in the non-transitory memory of the imaging system that when executed causes the processor of the imaging system to receive, via the user interface, a ground truth for the deep neural network. In a second example of the system optionally including the first example, the imaging system is further configured with executable instructions in the non-transitory memory of the imaging system that when executed causes the processor of the imaging system to transmit the ground truth to the server for training the central deep neural network. In a third example of the system optionally including one or more of the first and second examples, the server is configured with executable instructions in the non-transitory memory of the server that when executed cause the processor of the server to receive the intermediate representation and the ground truth, input the intermediate representation to a hidden layer of the central deep neural network as input features, and adjust weights of the hidden layer based on the ground truth. In a fourth example of the system optionally including one or more of the first through third examples, the intermediate representation of the imaging data comprises an output of a hidden layer of the deep neural network generated when the imaging data is input to the deep neural network.

In yet another embodiment, an imaging system comprises an x-ray source that emits a beam of x-rays towards a subject to be imaged, a detector that receives the x-rays attenuated by the subject, a data acquisition system (DAS) operably connected to the detector, and a computing device operably connected to the DAS and configured with executable instructions in non-transitory memory that when executed cause the computing device to: control the x-ray source to emit the beam of x-rays towards the subject; receive projection data from the DAS corresponding to the received x-rays attenuated by the subject; reconstruct an image from the projection data; input one of the projection data or the image to a deep neural network stored in the non-transitory memory; and transmit, to a server communicatively coupled to the computing device, an intermediate representation of the projection data or the image for training a central deep neural network stored in the server, the intermediate representation generated by a hidden layer of the deep neural network.

In a first example of the imaging system, the imaging system further comprises a display device coupled to the computing device, wherein the computing device is further configured with executable instructions in non-transitory memory that when executed cause the computing device to display, via the display device, the image and an output generated by the deep neural network from the projection data or the image. In a second example of the imaging system optionally including the first example, the imaging system further comprises an operator console coupled to the computing device, wherein the computing device is further configured with executable instructions in non-transitory memory that when executed cause the computing device to: receive, via the operator console, a ground truth for the deep neural network; and train the deep neural network without adjusting the hidden layer of the deep neural network according to an error calculated from the ground truth and the output generated by the deep neural network. In a third example of the imaging system optionally including one or more of the first and second examples, the computing device is further configured with executable instructions in non-transitory memory that when executed cause the computing device to transmit the ground truth to the server for training the central deep neural network. In a fourth example of the imaging system optionally including one or more of the first through third examples, the intermediate representation comprises an output of the hidden layer of the deep neural network.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
performing a scan of a subject to acquire imaging data;
inputting the imaging data to a deep neural network;
displaying an output of the deep neural network and an image reconstructed from the imaging data;

transmitting an intermediate representation of the imaging data generated by the deep neural network to a server for training a central deep neural network; and receiving a ground truth for the deep neural network, and transmitting the ground truth to the server for training the central deep neural network.

2. The method of claim 1, wherein the deep neural network comprises a first hidden layer and a second hidden layer, and wherein the intermediate representation comprises an output of the first hidden layer.

3. The method of claim 2, further comprising training the deep neural network based on an error of the output of the deep neural network, wherein training the deep neural network comprises adjusting weights of hidden nodes of the second hidden layer.

4. The method of claim 3, wherein training the deep neural network excludes training the first hidden layer.

5. The method of claim 1, wherein the ground truth is received from a user via a user interface of the imaging system.

6. The method of claim 1, further comprising training the deep neural network with backpropagation based on the ground truth.

7. The method of claim 1, further comprising reconstructing the image from the imaging data, wherein inputting the imaging data to the deep neural network comprises inputting the image to the deep neural network.

8. The method of claim 1, wherein displaying the output of the deep neural network and the image comprises displaying, via a display device of the imaging system, the output superimposed on the image.

9. The method of claim 1, wherein displaying the output of the deep neural network and the image comprises displaying, via a display device of the imaging system, the output of the deep neural network adjacent to the image.

10. A system, comprising:
an imaging system comprising a scanner for scanning a subject to acquire imaging data, a processor, and a non-transitory memory storing a deep neural network; and
a server comprising a processor and a non-transitory memory storing a central deep neural network, the server communicatively coupled to the imaging system via a network;
wherein the imaging system is configured with executable instructions in the non-transitory memory of the imaging system that when executed cause the processor of the imaging system to transmit an intermediate representation of the imaging data to the server for training the central deep neural network, the intermediate representation of the imaging data generated by the deep neural network; and
wherein the imaging system further comprises a user interface configured to receive input from an operator of the imaging system, wherein the imaging system is further configured with executable instructions in the non-transitory memory of the imaging system that when executed causes the processor of the imaging system to receive, via the user interface, a ground truth for the deep neural network.

11. The system of claim 10, wherein the imaging system is further configured with executable instructions in the non-transitory memory of the imaging system that when executed causes the processor of the imaging system to transmit the ground truth to the server for training the central deep neural network.

12. The system of claim 11, wherein the server is configured with executable instructions in the non-transitory memory of the server that when executed cause the processor of the server to receive the intermediate representation and the ground truth, input the intermediate representation to a hidden layer of the central deep neural network as input features, and adjust weights of the hidden layer based on the ground truth.

13. The system of claim 10, wherein the intermediate representation of the imaging data comprises an output of a hidden layer of the deep neural network generated when the imaging data is input to the deep neural network.

14. An imaging system, comprising:
an x-ray source that emits a beam of x-rays towards a subject to be imaged;
a detector that receives the x-rays attenuated by the subject;
a data acquisition system (DAS) operably connected to the detector; and
a computing device operably connected to the DAS and configured with executable instructions in non-transitory memory that when executed cause the computing device to:
control the x-ray source to emit the beam of x-rays towards the subject;
receive projection data from the DAS corresponding to the received x-rays attenuated by the subject;
reconstruct an image from the projection data;
input one of the projection data or the image to a deep neural network stored in the non-transitory memory; and
transmit, to a server communicatively coupled to the computing device, an intermediate representation of the projection data or the image for training a central deep neural network stored in the server, the intermediate representation generated by a hidden layer of the deep neural network.

15. The imaging system of claim 14, further comprising a display device coupled to the computing device, wherein the computing device is further configured with executable instructions in non-transitory memory that when executed cause the computing device to display, via the display device, the image and an output generated by the deep neural network from the projection data or the image.

16. The imaging system of claim 15, further comprising an operator console coupled to the computing device, wherein the computing device is further configured with executable instructions in non-transitory memory that when executed cause the computing device to:
receive, via the operator console, a ground truth for the deep neural network; and
train the deep neural network without adjusting the hidden layer of the deep neural network according to an error calculated from the ground truth and the output generated by the deep neural network.

17. The imaging system of claim 16, wherein the computing device is further configured with executable instructions in non-transitory memory that when executed cause the computing device to transmit the ground truth to the server for training the central deep neural network.

18. The imaging system of claim 14, wherein the intermediate representation comprises an output of the hidden layer of the deep neural network.

19. A method for an imaging system, comprising:
performing a scan of a subject to acquire imaging data;
inputting the imaging data to a deep neural network;

displaying an output of the deep neural network and an image reconstructed from the imaging data; and transmitting an intermediate representation of the imaging data generated by the deep neural network to a server for training a central deep neural network;

wherein the deep neural network comprises a first hidden layer and a second hidden layer, and wherein the intermediate representation comprises an output of the first hidden layer.

* * * * *